(12) United States Patent
Perreault (10) Patent No.: US 7,021,114 B2
(45) Date of Patent: Apr. 4, 2006

(54) STENT CRIMPER

(75) Inventor: Daniel Perreault, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 34 days.

(21) Appl. No.: 10/826,035

(22) Filed: Apr. 16, 2004

(65) Prior Publication Data
US 2005/0229670 A1   Oct. 20, 2005

(51) Int. Cl.
*B21D 41/00* (2006.01)

(52) U.S. Cl. ........................ 72/402; 29/283.5

(58) Field of Classification Search ............... 72/402; 29/237, 282, 283.5
See application file for complete search history.

(56) References Cited

U.S. PATENT DOCUMENTS

| | | | |
|---|---|---|---|
| 565,257 A | 8/1896 | Boyd | |
| 758,195 A | 4/1904 | Schweinert et al. | |
| 1,480,077 A * | 1/1924 | Johnson | 72/402 |
| 1,665,915 A | 4/1928 | Ekman | |
| 1,889,795 A | 12/1932 | Smith et al. | |
| 2,292,421 A | 8/1942 | Wolf | 29/88.2 |
| 2,751,077 A | 6/1956 | Latin et al. | 207/4 |
| 2,887,222 A | 5/1959 | Latin et al. | 207/4 |
| 2,986,192 A | 5/1961 | Macleod | 153/1 |
| 3,203,078 A * | 8/1965 | Ustin | 29/862 |
| 3,375,697 A * | 4/1968 | Arnold | 72/402 |
| 3,416,352 A | 12/1968 | Ribback et al. | 72/402 |
| 3,664,213 A | 5/1972 | Anati | 81/91 R |
| 3,695,087 A | 10/1972 | Tuberman | 72/402 |
| 3,731,518 A | 5/1973 | Blocher | 72/402 |
| 4,434,645 A | 3/1984 | Svercl et al. | 72/402 |
| 4,567,650 A | 2/1986 | Balyasny et al. | 29/822 |
| 4,578,982 A | 4/1986 | Schrock | 72/402 |
| 4,644,777 A * | 2/1987 | Kumeth | 72/402 |
| 4,854,031 A | 8/1989 | Eisenzimmer | 29/508 |
| 4,942,756 A | 7/1990 | Charzewski | 72/399 |
| 5,026,377 A | 6/1991 | Burton et al. | 606/108 |
| 5,138,864 A | 8/1992 | Tarpill | 72/410 |
| 5,183,085 A | 2/1993 | Timmermans | 140/89 |
| 5,243,846 A | 9/1993 | Davis et al. | 72/402 |
| 5,261,263 A | 11/1993 | Whitesell | 72/410 |
| 5,262,263 A | 11/1993 | Ohkawa et al. | 430/66 |
| 5,381,686 A | 1/1995 | Thorup | 72/453.06 |
| 5,411,521 A * | 5/1995 | Putnam et al. | 606/225 |

(Continued)

FOREIGN PATENT DOCUMENTS

JP    55-103216    *   8/1980    ............ 72/402

(Continued)

OTHER PUBLICATIONS

U.S. Appl. No. 10/788,088, filed Feb. 26, 2004, Weber et al.

*Primary Examiner*—Daniel C. Crane
(74) *Attorney, Agent, or Firm*—Vidas, Arrett & Steinkraus, PA (57) ABSTRACT

An apparatus for applying an inward force to a medical device may include at least two independently operable sections. Each section may include a plurality of movable blades arranged to form an aperture or chamber whose size may be varied. Each blade may be pivotally connected to a mount and slidably engaged with a constraining member. The blades are movable so as to allow the aperture to be sized to contain the medical device and to alter the size of the aperture.

29 Claims, 8 Drawing Sheets

U.S. PATENT DOCUMENTS

| | | | |
|---|---|---|---|
| 5,437,083 A | 8/1995 | Williams et al. | 29/235 |
| 5,509,184 A | 4/1996 | Herrero | 29/252 |
| 5,546,646 A | 8/1996 | Williams et al. | 29/407.08 |
| 5,626,604 A | 5/1997 | Cottone, Jr. | 606/198 |
| 5,630,830 A | 5/1997 | Verbeek | 606/198 |
| 5,672,169 A | 9/1997 | Verbeek | 606/1 |
| 5,692,294 A | 12/1997 | Casey | 29/753 |
| 5,715,723 A | 2/1998 | Owens | 72/402 |
| 5,725,519 A | 3/1998 | Penner et al. | 606/1 |
| 5,738,674 A | 4/1998 | Williams et al. | 606/1 |
| 5,746,764 A | 5/1998 | Green et al. | 606/194 |
| 5,752,405 A | 5/1998 | Gerst et al. | 72/312 |
| 5,810,873 A | 9/1998 | Morales | 606/198 |
| 5,836,952 A | 11/1998 | Davis et al. | 606/108 |
| 5,860,966 A | 1/1999 | Tower | 606/1 |
| 5,893,852 A | 4/1999 | Morales | 606/108 |
| 5,911,752 A | 6/1999 | Dustrude et al. | 623/1 |
| 5,920,975 A | 7/1999 | Morales | 29/282 |
| 5,931,851 A | 8/1999 | Morales | 606/194 |
| 5,951,540 A | 9/1999 | Verbeek | 606/1 |
| 5,974,652 A | 11/1999 | Kimes et al. | 29/516 |
| 5,992,000 A | 11/1999 | Humphrey et al. | 29/516 |
| 6,009,614 A | 1/2000 | Morales | 29/516 |
| 6,018,857 A | 2/2000 | Duffy et al. | 29/407.01 |
| 6,051,002 A | 4/2000 | Morales | 606/108 |
| 6,063,102 A | 5/2000 | Morales | 606/198 |
| 6,074,381 A | 6/2000 | Dinh et al. | 606/1 |
| 6,082,990 A | 7/2000 | Jackson et al. | 425/517 |
| 6,108,886 A | 8/2000 | Kimes et al. | 29/280 |
| 6,125,523 A | 10/2000 | Brown et al. | 29/516 |
| 6,141,855 A | 11/2000 | Morales | 29/516 |
| 6,167,605 B1 | 1/2001 | Morales | 29/282 |
| 6,176,116 B1 * | 1/2001 | Wilhelm et al. | 72/409.12 |
| 6,240,615 B1 | 6/2001 | Kimes et al. | 29/516 |
| 6,309,383 B1 | 10/2001 | Campbell et al. | 606/1 |
| 6,352,547 B1 | 3/2002 | Brown et al. | 606/198 |
| 6,360,577 B1 | 3/2002 | Austin | 72/402 |
| 6,387,117 B1 | 5/2002 | Arnold, Jr. et al. | 623/1.1 |
| 6,481,262 B1 | 11/2002 | Ching et al. | 72/416 |
| 6,568,235 B1 | 5/2003 | Kokish | 72/402 |
| 6,629,350 B1 | 10/2003 | Motsenbocker | 29/283.5 |
| 6,651,478 B1 | 11/2003 | Kokish | 72/402 |
| 6,823,576 B1 * | 11/2004 | Austin | 29/516 |
| 6,840,081 B1 * | 1/2005 | Kokish | 72/402 |
| 2002/0035774 A1 | 3/2002 | Austin | 29/516 |
| 2002/0138996 A1 | 10/2002 | Ohtomo et al. | 33/286 |
| 2002/0161426 A1 | 10/2002 | Iancea | 623/1.11 |
| 2003/0056360 A1 | 3/2003 | Brown et al. | 29/516 |
| 2003/0150250 A1 | 8/2003 | Shortt | 72/235 |
| 2003/0192164 A1 | 10/2003 | Austin | 29/505 |

FOREIGN PATENT DOCUMENTS

| | | | | |
|---|---|---|---|---|
| SU | 144914 | * | 1/1962 | 72/402 |
| SU | 437561 | * | 7/1974 | 72/402 |

* cited by examiner

STENT CRIMPER

BACKGROUND OF THE INVENTION

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are available in both self-expanding and inflation or balloon expandable configurations. Inflation expandable stents are well known and widely available in a variety of designs and configurations. Both self-expanding and inflation expandable stents are typically crimped to their reduced configuration after being disposed about a delivery catheter. They are maneuvered to the deployment site and expanded to the vessel diameter either by fluid inflation of a balloon positioned between the stent and the delivery catheter, or upon release of the self-expanding stent from its crimped state, typically from a retaining sleeve.

Stents that are not properly secured or retained to the catheter may slip and either be lost or be deployed in the wrong location or partially deployed. Therefore, it is important that they be properly secured to or retained on or about the catheter. In securing a stent to a catheter, however, the stent must be crimped in such a way as to minimize or prevent altogether distortion of the stent and to thereby prevent abrasion and/or reduce trauma of the vessel walls.

Devices for reducing the diameter of stents are generally known, such as described in U.S. Pat. No. 6,360,577 to Austin, the entire disclosure of which is incorporated herein by reference.

Self-expanding stents offer some unique challenges when being loaded on a catheter in part because they have a tendency to open of their own volition at ambient conditions. Thus, it is common practice when loading a self-expanding stent onto a catheter, to constrain only one half of the length of a strut at one time. This is more time and labor intensive because it requires reducing the diameter of the stent a little bit of the stent at a time.

It would be desirable to be able to crimp a stent in sections of varying diameter depending on how one would desire the stent to deploy.

There remains a need in the art for a crimping device that provides more flexibility during the crimping process.

SUMMARY OF THE INVENTION

It would be desirable to produce a device capable of crimping a stent while minimizing the distortion of, and scoring and marking of the stent due to the crimping. The present invention is directed, in at least one aspect, to that end.

The present invention relates generally to an apparatus and method for reducing an article, such as a medical device, in size. Suitable medical devices include stents, stent-grafts, grafts, vena cava filters and the like, whether self-expandable or balloon expandable or otherwise expandable, although the apparatus may also be employed with any other suitable, generally tubular medical devices which must be reduced in size. Thus, the apparatus described herein may be used to reduce the size of any suitable expandable medical device.

It is further understood that the invention contemplates crimping a medical device either directly to or about a catheter tube or to a catheter balloon which is disposed about a catheter tube. When reference is made to crimping a medical device about a catheter, a balloon may be situated between the medical device and the catheter tube or the medical device may be disposed directly about a region of a catheter tube. The invention also contemplates crimping a stent in the absence of a catheter.

The apparatus according to the present invention is designed for applying inward or constraining forces to a medical device. In its simplest form, the apparatus includes at least one independently operable crimping section, each section further including at least three movable blades. The blades may be arranged to form an aperture or chamber whose size may be varied by moving the blades. The blades are further pivotally connected to a rotatable mount. Rotation of the mount may cause a change in the size of the chamber.

The mount may allow for very thin crimping sections of as little as about 1–2 mm in width.

In another embodiment, the apparatus includes at least two independently operable, discrete crimping sections. Such a device allows for crimping of a medical device such that it has varying diameters along its length.

In another embodiment, the apparatus includes at least three independently operable discrete crimping sections.

The device may include as many as 40–80 independently operable discrete crimping sections.

Desirably, when the apparatus comprises multiple crimping sections, each section has a thickness or width of about 1–2 mm.

Each section may have its own actuation or drive device which is capable of rotating the mount or otherwise causing the blades to move, thereby altering the size of the chamber. In some embodiments, multiple crimping sections may be arranged to be driven by a common drive device.

In one embodiment, the drive device is pneumatic. A pneumatic drive device may be beneficial and superior to other drive devices when crimping medical devices at cryogenic temperatures.

In one embodiment, the device includes at least three independently operable crimping sections, each crimping section further including a mount and at least three blades arranged to form a chamber whose size may be varied. Each section may be in communication with an actuation device which is capable of causing the mount and blades to move such that the size of the chamber is altered. Each section may have its own actuation device. Each crimping section may form a separate chamber, and each section may be independently driven such that the chambers of each section may increased and/or decreased independently of one another. Thus, the apertures of the independent sections may be controlled such that various cross-sections of the resultant crimped stent have different diameters.

Any type of actuation device known in the art may be employed herein. Actuation of the independent sections may be accomplished by hand, or the sections may be automatically actuated, such as by a control system. Actuation devices may include any combination of motors such as electric motors, gear systems such as spline gears, belts, frictional methods using rubber strips, magnets with linear induction motors or magnets with direct-current gearhead motors, tabs for manual drives, pneumatic actuation devices, air compressors, and so forth. The use of separate sections allows for different sections of the medical device to be independently crimped resulting in a medical device with a cross-section which may vary in one or more portions of the medical device.

In one embodiment, each crimping section may include a mount or retaining ring, to which each of a plurality of blades may be pivotally mounted. The blades may be arranged to form a chamber. Each blade may further include an aperture or slot of a predetermined size which may be arranged to receive a blade constraining member. The mount may be rotated while the blade constraining member remains stationary. Each blade may receive a separate blade constraining member. Upon rotation of the mount, the pivot point of each blade may translocate with the mount. The interaction of each blade with the blade constraining member causes each blade to pivot about its pivot point to vary the size of the chamber. The bounds of the aperture or slot may determine the travel path of the blade, and the maximum and/or minimum chamber size. Thus, changing the length of the slot may change the amount of allowable blade movement and mount rotation, as well as the maximum and/or minimum chamber size.

The mount may be actuated using any means known in the art. Motors such as electric motors may be employed or manual actuation may be employed. The actuation device may include a spline gear. In such an embodiment, each crimping section has a set of teeth which mesh with the spline gear.

Cam gear systems may be employed. These types of systems are described in commonly assigned U.S. Pat. No. 6,360,577, which is incorporated by reference herein in its entirety.

Pneumatic actuation devices are described for use in U.S. Pat. No. 5,752,405 which is incorporated by reference herein in its entirety.

Yet another embodiment may include friction contact drive rollers in which the outer surface of the crimping section may incorporate a strip of rubber.

In yet another embodiment, magnets may be employed in combination with linear induction drive motors. This embodiment offers the advantage of being frictionless as well as having no bearings resulting in very smooth motion.

Other systems include belt-driven systems, and tabs where manual operation may be used.

In any of the above embodiments, each section may be manually driven, or may be driven by use of electric motor(s), air cylinder(s), pneumatic screw(s), and so forth. Each crimping section may have its own motor, air cylinder, pneumatic screw, and so forth.

Using the device according to the present invention, a medical device may be reduced in size by placing it in the aperture formed by the blades, and then moving the blades such that an inward force is applied to the device. In some embodiments, each blade may apply a substantially equal amount of force to a medical device. As noted above, the blades are moved inward either manually, or by the use of a suitable actuation device.

Independent crimping sections which are independently operable allow an operator to selectively and independently crimp and/or release specific areas of a medical device being shaped, and allow for variable pressure to be applied to different sections of the medical device, and for the diameter of the medical device to be more readily varied. Thus, it is within the scope of the invention to crimp a stent, for example, by placing it in the device, and crimping to a smaller diameter at each end than in the middle. In such an embodiment of the invention, the end sections of the device may be operated to produce smaller apertures. A further benefit of having independently operable sections is that the entire medical device does not have to pass through an entire iris with a single diameter, as in prior art devices, a benefit which is even more notable for medical devices which have drug coatings which could otherwise be marred or scraped off the stent. For examples, sections of the crimper may be opened sequentially to facilitate removal of the stent from the crimper.

Each section may further be coupled with its own actuation device, or a single actuation device may be designed to independently control each crimping section. Suitable actuation devices include any known to those of skill in the art including hand operated actuation devices as well as automatic actuation devices including motors and gear systems. In one embodiment, independent electric motors are in communication with each crimping section.

In various embodiments, the inventive device may also be used as a variable size and/or variable shape balloon mold. Thus, the invention is further directed to a method of forming a medical balloon.

The invention is also directed to a method of manipulating a medical device which includes the steps of providing a medical device and providing at least two crimping sections, each section including at least three blades capable of applying an inward force. The blades are disposed about a reference circle to form a shrinkable aperture. A medical device such as a stent, is placed into the shrinkable aperture of each crimping section, and the blades from each crimping section are simultaneously moved inward to apply a radial inward force to the medical device. Each section may, however, be independently actuated and controlled such that the blades from one crimping section may or may not simultaneously move with the blades from another crimping section. Thus, different parts of the medical device may be crimped to the same or different diameters at the same or different times. The crimping sections are suitably configured and arranged such that the aperture is substantially continuous.

There is no minimum constraint on how narrow each section may be. For example, each section may be the same width as a strut of the stent, but there is not limitation as to what the width of each section may be.

The inventive apparatus may also be used as a variable size balloon mold. To that end, the invention is further directed to a method of molding a medical balloon. In the practice of the method, a balloon preform prepared through any suitable technique known in the art is provided. The preform is placed in an apparatus which has a shrinkable tubular aperture formed by at least three movable blades disposed about a reference tube. The aperture may be set to a predetermined size prior to placement of the preform therein or after placement of the preform therein. An inflation fluid is supplied to the balloon preform to expand the balloon preform until it contacts the blades. The preform may optionally be heated prior to, during or after the blowing step. The thus formed balloon is then pressure relieved and removed from the apparatus.

DETAILED DESCRIPTION OF THE INVENTION

While this invention may be embodied in many different forms, there are described in detail herein by way of illustration, specific embodiments of the invention. This description is an exemplification of the principles of the invention and is not intended to limit the invention to the particular embodiments illustrated.

Any U.S. patents, U.S. applications and all other published documents mentioned anywhere in this application are incorporated herein by reference in their entireties.

The term crimping, as used herein, refers to a reduction in size or profile of an article, such as a medical device.

In the description that follows it is understood that the invention contemplates crimping a medical device either directly about a catheter tube or to a catheter balloon which is disposed about a catheter tube. When reference is made to crimping a medical device about a catheter, a balloon may be situated between the medical device and the catheter tube or the medical device may be crimped to a region of a catheter tube directly. The invention also contemplates crimping a stent in the absence of a catheter to reduce the stent in size.

Figure 1:
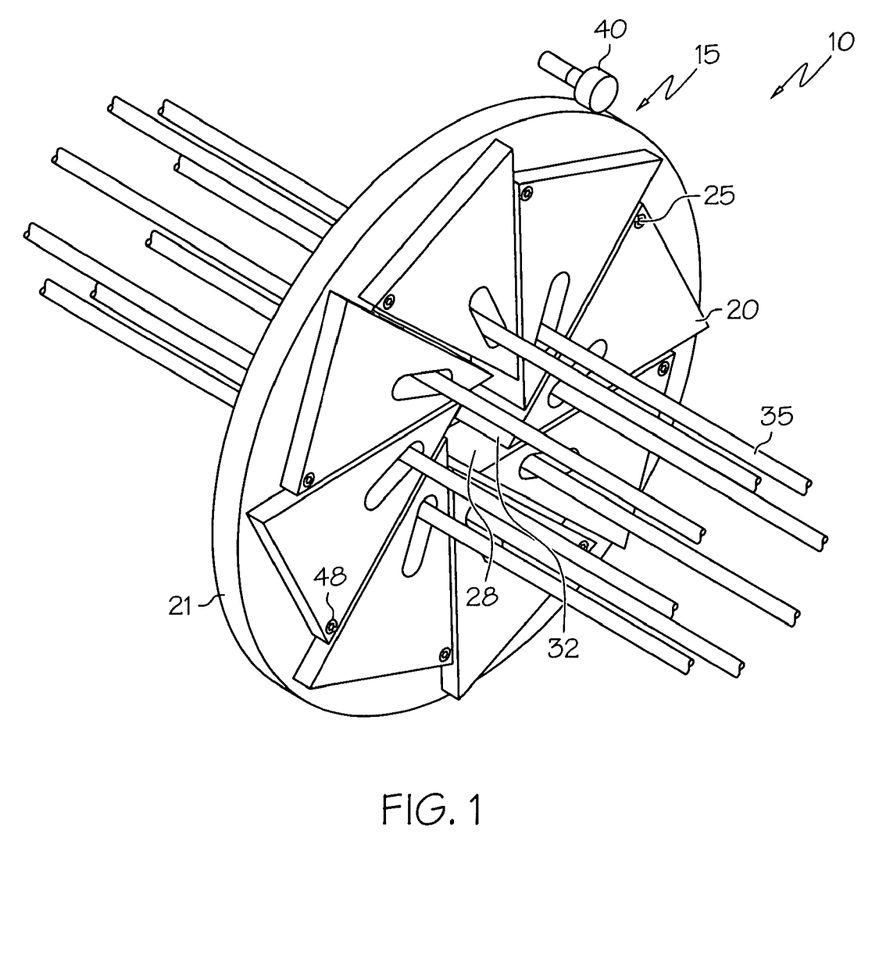
FIG. 1 is a perspective view of an embodiment of the inventive crimping device.
Figure 2:
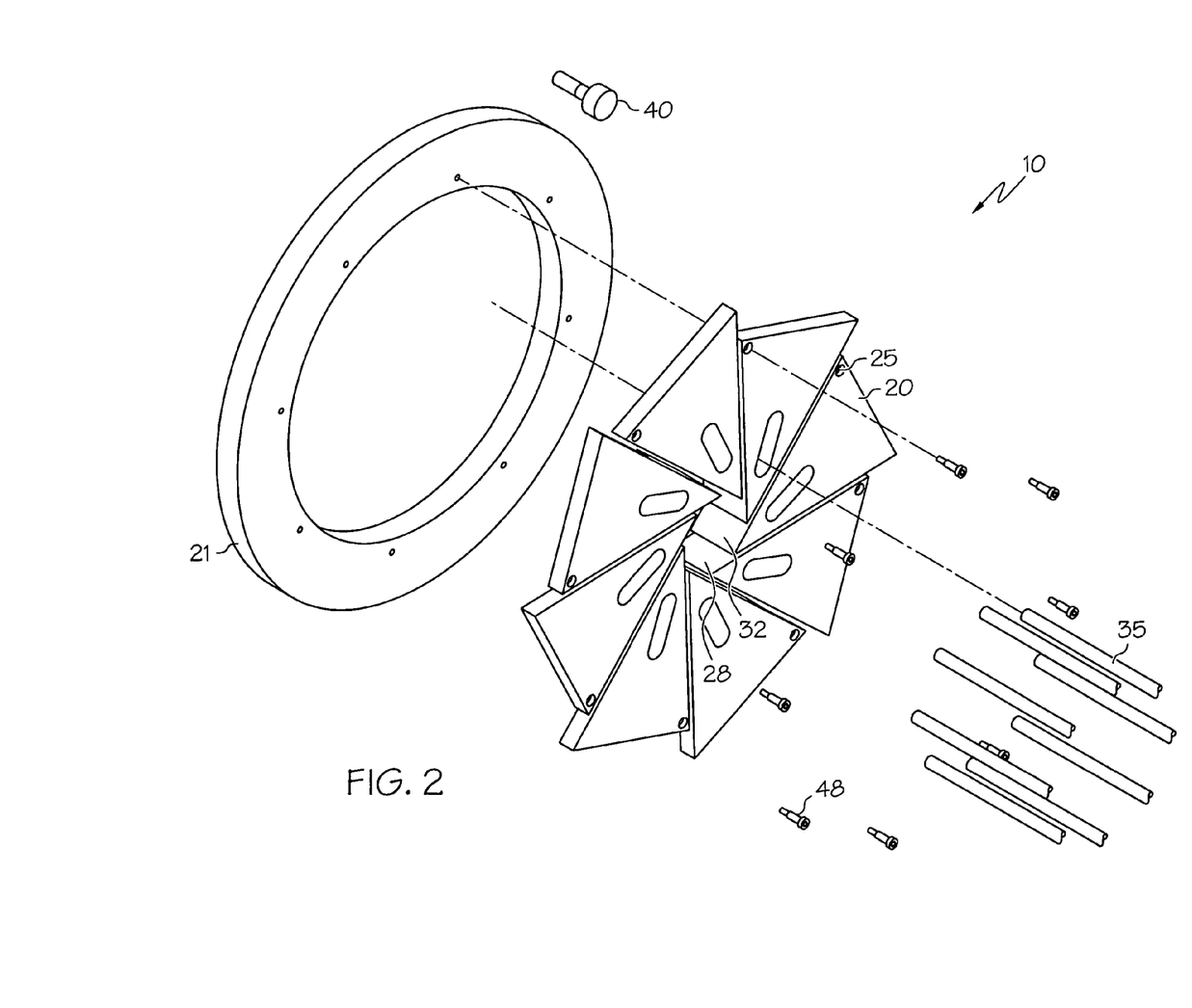
FIG. 2 is an exploded view of an embodiment of the inventive crimping device.

FIGS. 1 and 2 depict an embodiment of a crimping device 10 according to the present invention. The device 10 may have a crimping section 15 comprising a rotatable mount 21, a plurality of movable blades 20 and at least one blade constraining member 35. As shown, one blade constraining member 35 is provided for each blade 20. The mount 21 may be rotatable about a central axis, and may be rotated by a drive device 40. The blades 20 may be arranged to form an aperture or chamber 28 having a length and cross-sectional area. The blades 20 may be equally spaced about the mount 21. Wall surface portions of the blades 20 which bound the chamber 28 may comprise a contacting surface 32 and may contact an article placed within the chamber 28. Wall surfaces or contacting surfaces 32 which bound the chamber 28 may collectively comprise an iris. Desirably, an iris is orthogonal to the central longitudinal axis of the chamber 28. A zero point may be the center point of an iris. A plurality of zero points may lie along the central longitudinal axis of the chamber 28. The central longitudinal axis of the chamber 28 may correspond with the central axis of the mount 21. In some embodiments, a mount 21 may have an annular shape or may comprise a retaining ring.

The shape of an iris, or a cross-section of the chamber 28, is dependent upon the shape of the blades 20. In some embodiments, an iris may be in the shape of a regular polygon, wherein all sides and all interior angles of the iris are the same. In some embodiments, the iris may be a non-regular polygon. In some embodiments, the iris may have a curved, non-polygonal shape, such as a circle.

Each blade 20 may be pivotably secured to the mount 21 at a pivot point 25. The pivoting axis of each blade 20 may be parallel to the longitudinal axis of the chamber 28. A fastener 48, such as a pin, screw, bolt or the like may be used to secure a blade 20 to the mount 21.

Figure 3:
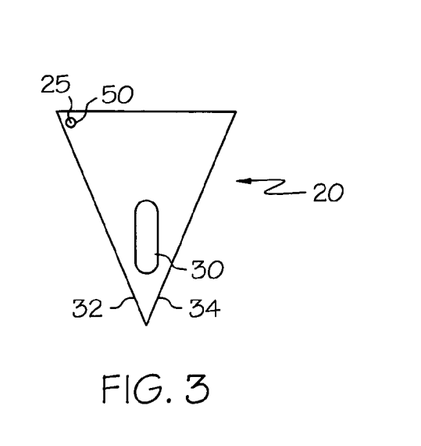
FIGS. 3 and 4 show an embodiment of a blade.
Figure 4:
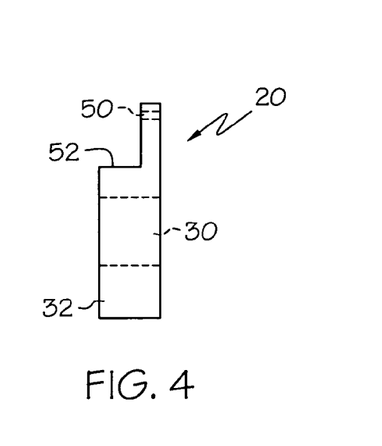

FIGS. 3 and 4 show a detail of one embodiment of a blade 20. The blade 20 may include a first aperture 50 for receiving a fastener. When secured to the mount 21, a blade 20 may pivot about the central axis of the first aperture 50. A blade 20 may include a second aperture 30 for receiving a blade constraining member. In some embodiments, the second aperture 30 may comprise a slot or have an elongated oval shape. A second aperture 30 may also be provided in other elongate shapes. A second aperture 30 is desirably dimensioned to interact with a blade constraining member 35 to guide the blade 20 as the mount 21 is rotated. The width of a second aperture 30 may be slightly larger than the diameter or appropriate width dimension of a blade constraining member 35. The length of a second aperture 30 may be substantially larger than the diameter or appropriate width or height dimension of a blade constraining member 35, as the second aperture 30 may translocate with respect to the blade constraining member 35 as the blade 20 shifts position upon rotation of the mount 21.

A blade 20 may further include a notched portion 52. A portion of the mount 21 may be oriented within the notched portion 52 when the blade is attached to the mount 21, allowing at least a portion of the contacting surface 32 of the blade 20 to be located within the internal volume of the mount 21. Thus, at least a portion of a chamber 28 formed by a plurality of blades 20 may be located within the internal volume of the mount 21.

Referring again to FIGS. 1 and 2, in some embodiments, a blade constraining member 35 may comprise an elongate member, such as a tube or rod. A blade constraining member 35 may have any cross-sectional shape, and desirably has a curved cross-sectional shape, such as a circle or an ellipse. At least a portion of each blade constraining member 35 may be oriented within a second aperture 30 or slot of a blade 20. In some embodiments, a blade constraining member 35 may extend through both sides of a blade 20. Desirably, each blade constraining member 35 will remain globally fixed in position as the mount 21 and blades 20 shift positions respectively.

Figure 5:
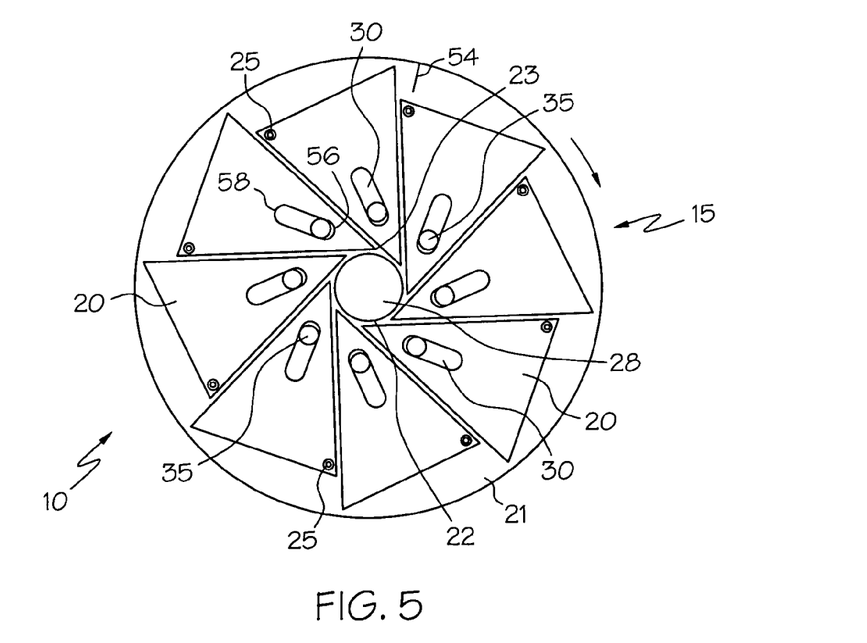
FIG. 5 is an elevational view of an embodiment of the inventive crimping device having a first chamber configuration.
Figure 6:
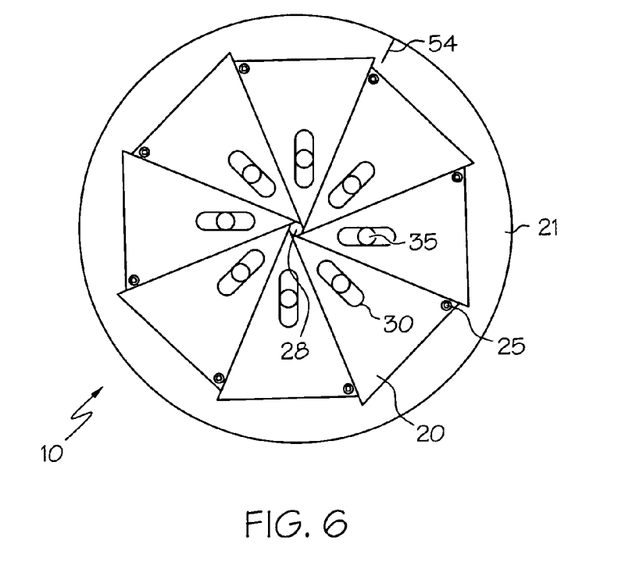
FIG. 6 is an elevational view of an embodiment of the inventive crimping device having another chamber configuration that is more closed than the chamber shown in the embodiment in FIG. 5.

FIG. 5 shows an embodiment of the device 10 having a first chamber 28 size with the mount 21 at a first rotational orientation. FIG. 6 shows an embodiment of the device 10 with the mount 21 at a second rotational orientation, wherein the resulting shift blade 20 positions has caused the chamber to change size. A reference line 54 is shown on the mount 21 in FIGS. 5 and 6 to show a change in rotational orientation. As the mount 21 is rotated, such as by hand or by a drive device, the pivot point 25 of each blade 20 displaces with the mount 21. The blade constraining members 35 within the second apertures 30 of the blades 20 remain fixed in position and therefore bear upon the blades 20, thereby causing each blade 20 to rotate about its pivot point 25 and also causing the size of the chamber 28 to increase or decrease according to the direction of rotation of the mount 21. It should be noted that the embodiment of FIG. 6 includes a blade configuration wherein adjacent blades contact one another, while the embodiment of FIG. 5 includes blades that do not contact adjacent blades. Both embodiments exhibit the desired change in chamber 28 size upon rotation of the mount 21, and both are suitable for crimping an article placed within the chamber 28.

Figure 7:
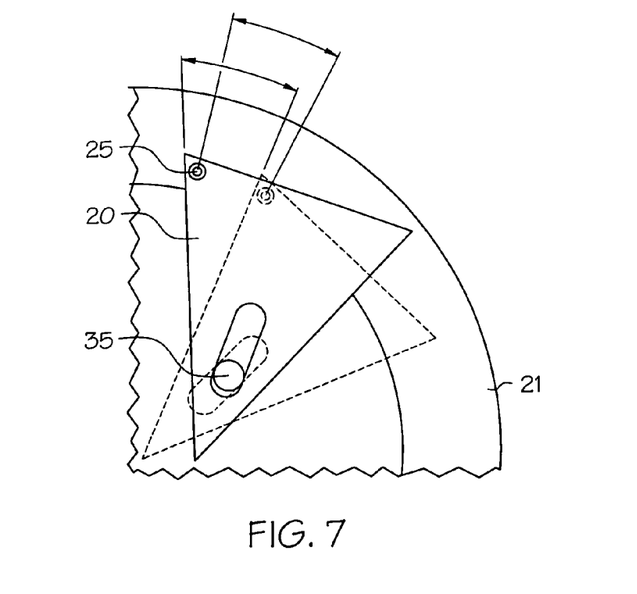
FIG. 7 illustrates the movement of a blade as the chamber size is varied.

FIG. 7 illustrates in detail the shift in position a blade 20 may experience when the mount 21 is rotated. The pivot point 25 of the blade 20 may displace according to the rotation of the mount 21. As the pivot point 25 of a blade displaces, constraining forces applied to the blade 20 by the blade constraining member 35 cause the blade 20 to pivot about the pivot point 25. The shifted position of the blade 20 after rotation of the mount 21 is shown in phantom lines.

Each blade 20 may be made of any suitable material including plastics and metals. Typically, hard material including hardened steel will be used. Desirably, the blades 20 will be made of a material such as zirconia ceramic. Blades 20 made of zirconia ceramic may be used without lubrication. Furthermore, because of their low thermal conductivity, they may be used to create a highly insulated chamber 28 suitable for the cryogenic processing of shape memory alloy (SMA) articles, such as stents, at or below the martinsitic finish temperature. For example, the chamber may be maintained at a temperature of about negative 80° C., and a stent formed of a SMA, such as nitinol, may be inserted therein. Upon equilibration of the temperature of the stent, the blades may be moved inward to reduce the diameter of the stent. The stent is thus reduced in diameter while being maintained in the martensitic state. In such an embodiment, a SMA stent may be disposed between the blades 20, which are cooled by a source of cooling fluid. It is possible to also provide a second source of cooling fluid at the opposite end of the blades as the first source. The cooling fluid may be a liquid cryogenic. Exemplary cryogenics include liquid nitrogen, argon or carbon dioxide although other cryogens may also be used. The cooling fluid may also be a chilled gas such as air. The cooling fluid may also be a cooled inert gas such as nitrogen, argon or other inert gasses. This is also described in U.S. Pat. No. 6,360, 577. Other materials which would be of use in embodiments in which the blades are chilled include Inconel® and the like.

In various embodiments, each crimping section 15 may include as few as three blades 20, and as many as sixteen or more blades 20. The maximum number of blades 20 is limited only by the relevant size and strength constraints, as each blade 20 may be as small as possible while also having the strength to perform a crimping operation without experiencing deformation. In some embodiments the blades 20 may be pie-shaped wedges.

Each crimping section 15 may have a chamber 28 having a length. The length of each chamber 28 may be dependent upon the dimension of the blades 20 along the length of the chamber 28, and may range from as small as possible to greater than the length of a medical device or article being crimped or shaped. For example, the length of a chamber 28 may range from less than 1 mm to over 20 mm. In some embodiments, a chamber 28 may have a length of about 1 mm to about 2 mm.

Referring to FIG. 5, in some embodiments, the blades 20 may be disposed about a reference circle 22 to form a chamber 28 whose size may be varied. In some embodiments, the chamber 28 size may be limited to a maximum size and a minimum size. The maximum and minimum sizes of the chamber 28 may be controlled by the second apertures 30 of the blades 20. As a mount 21 rotates and the size of a chamber 28 is varied, the second aperture 30 of a blade 20 shifts with respect to the blade constraining member 35 oriented within the second aperture 30. The blade constraining member 35 will travel along the length of the second aperture 30. Movement of the blade 35 may be stopped if the blade constraining member 35 abuts an end of the second aperture 30. Therefore, a first end 56 of the second aperture 30 may limit the maximum size of the chamber 28. A second end 58 of the second aperture 30 may limit the minimum size of the chamber 28, and in some embodiments, the second end 58 may be placed such that the chamber 28 is prevented from fully closing.

In some embodiments, for example as shown in FIG. 6, the blades 20 may be arranged to contact or be slidably engaged with one another. In such embodiments, a first blade 20 may include a second aperture 30, and a single blade constraining member 35 may be used. Upon rotation of the mount 21, the blade constraining member 35 may cause the first blade 20 to pivot about its pivot point 25, and the sliding engagement between all of the blades 20 will cause the remaining blades to pivot accordingly.

In some embodiments, when the chamber 28 is fully closed, all of the blade 20 tips may meet at a zero point or at the central longitudinal axis of the device.

In some embodiments, a chamber 28 may be open in a first configuration, and the mount 21 may be rotated to close the chamber 28. Upon continued rotation of the mount 21, a chamber 28 may reopen in another configuration or a second configuration. Each blade 20 may have a first contacting surface 32 which may bound the chamber 28 in the first configuration. Each blade 20 may have a second contacting surface 34 (see FIG. 3) which may bound the chamber 28 in the second configuration.

Figure 8:
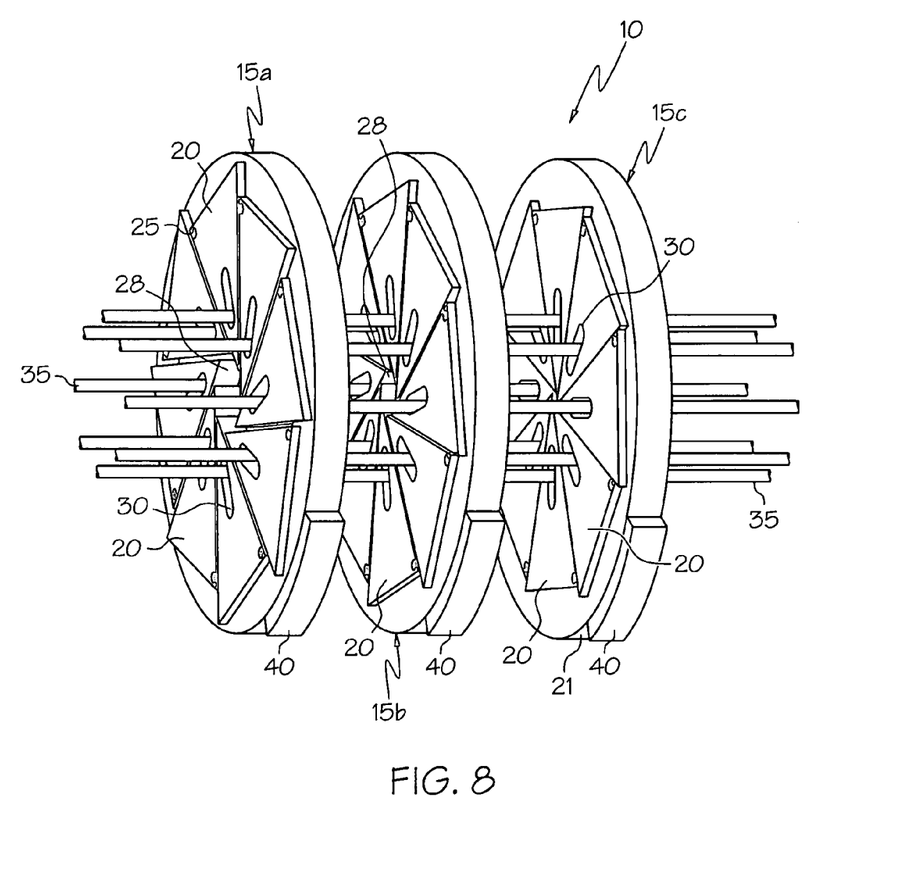
FIG. 8 shows another embodiment of the device having multiple independently adjustable crimping sections.

FIG. 8 shows another embodiment of an inventive device 10 having multiple crimping sections 15. As depicted, a first crimping section 15a may include a fully open chamber 28, a second crimping section 15b may include a partially open chamber 28, and a third crimping section 15c may have a chamber 28 that is nearly closed. Each crimping section 15 may be independently operable, and thus the chamber 28 size of each crimping section 15 may be opened and/or closed independently from all other sections 15. Although the embodiment shown includes spacing between the individual crimping sections 15, various embodiments may include crimping sections 15 that are immediately adjacent to one another along the length of the device.

Each crimping section 15 may include a mount 21 and a plurality of blades 20 as previously discussed. As shown, common blade constraining members 35 extend through each crimping section 15. Each blade constraining member 35 may extend through one blade 20 of each crimping section 15. In an embodiment wherein the blades 20 of each crimping section 15 are slidably engaged with one another, a single blade constraining member 35 may be used for all of the crimping sections 15. Each crimping section 15 may be actuated independently using its own actuation or drive device 40.

Actuation may be accomplished using any means known in the art including manual or automatic actuation. Actuation or drive devices may include, for example, motors, gear systems including spline gears, frictional methods such as rubber strips, belts, tabs for manual actuation, magnets with linear induction motors which incorporate bearings for smooth rotation, pneumatic screws, air cylinders, or any combination thereof. A drive device 40 may further include linear motors available from Anorad Navigation, such as the LE Vacuum Compatible Linear Motor and PCLM Piezo Motor models; linear motor tables available from Parker Automation, such as the LXR series tables; and walking motor technology, such as PiezoLEGS motors available from PiezoMotor Uppsala AB, Sylveniusgatan 5D SE-754 50 Uppsala, Sweden. PiezoLEGS motors are available is sizes as small as 1 mm in width. In some embodiments, drive devices 40 may be suitable for use in nonmagnetic, vacuum and/or clean environments, and be insulated against high and low temperatures to which the device 10 may be exposed.

Although the device 10 shown in FIG. 8 includes 3 independently operable crimping sections 15, other embodiments of the device 10 may include 4, 5, 6, 7, up to 80 or more independently operable crimping sections 15. It is also important to note that while the crimping sections 15 are desirably independently operable, there may be situations under which it is desirable that multiple crimping sections 15 operate together.

Figure 9:
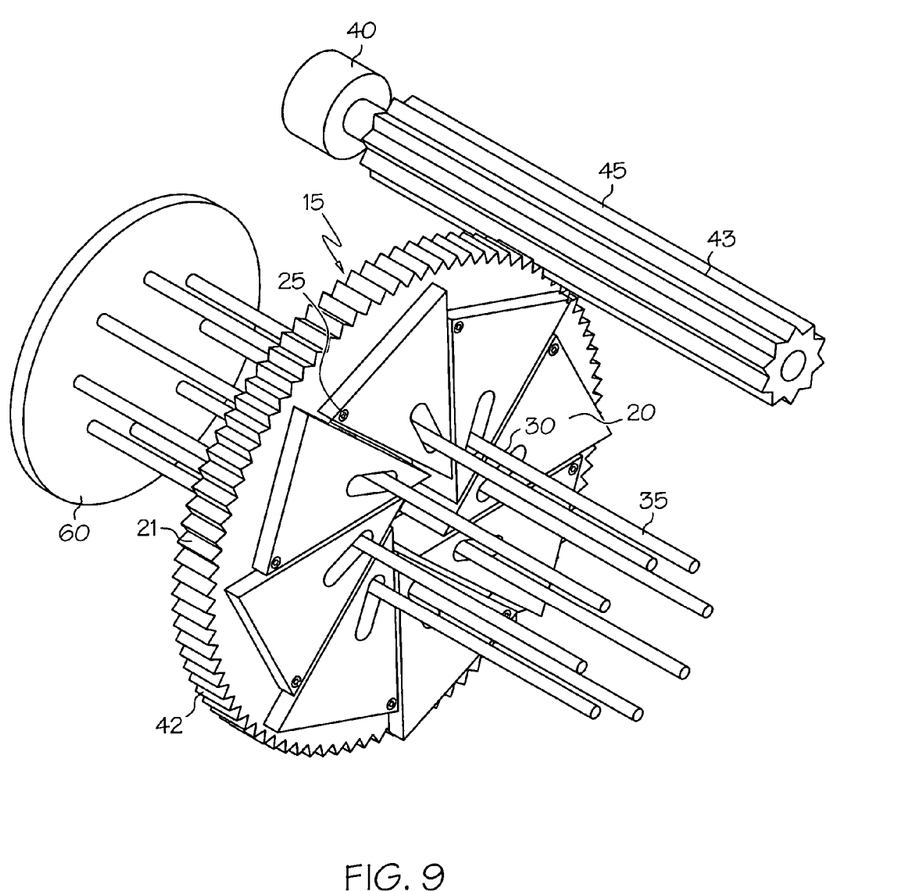
FIG. 9 shows another embodiment of the device having a spline gear system.

FIG. 9 illustrates generally at 15 a single crimping section in which a drive device 40 includes a spline gear 45 system. The mount 21 may comprise a gear and include teeth 42 which fit in corresponding teeth 43 in the spline gear 45. When the spline gear is rotated, the mount 21 will rotate. The blades 20 will move pivotally around their pivot point 25 but are constrained by blade constraining members 35 inserted through slots 30 in blades 20 as previously discussed. FIG. 9 further shows the blade constraining members 35 fixed to a stationary mount 60.

Figure 10:
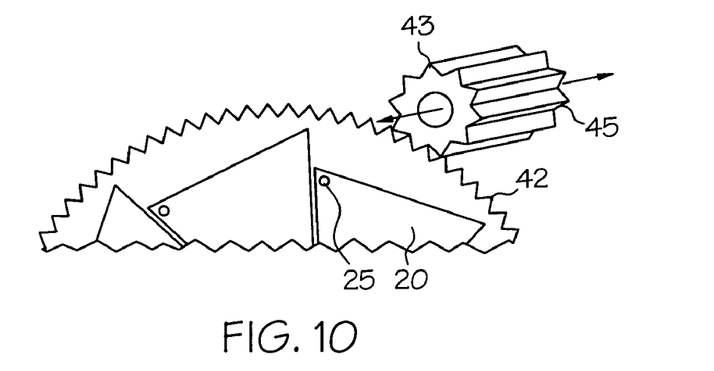
FIG. 10 shows another view of a spline gear system.

Optionally, the spline gear 45 may be slidably mounted so that it may slide along or parallel to the longitudinal axis of the device 10 and engage the other crimping sections 15 that may be included in the device 10. FIG. 10 depicts another view showing the teeth 42 of the retaining ring 21 in combination with the teeth 43 of the spline gear 45, and movement of the spline gear 45.

Figure 11:
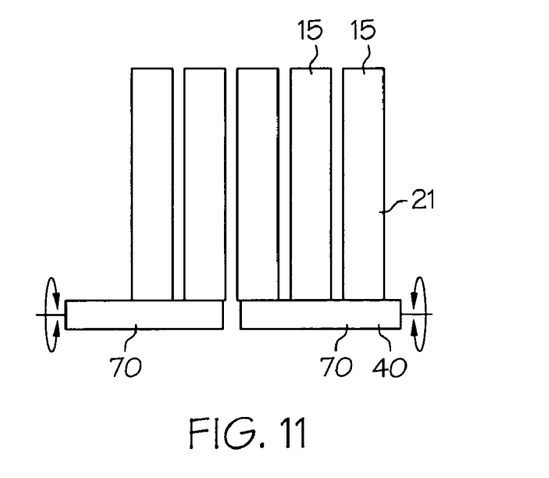
FIG. 11 illustrates an embodiment having frictional drive rollers.
Figure 12:
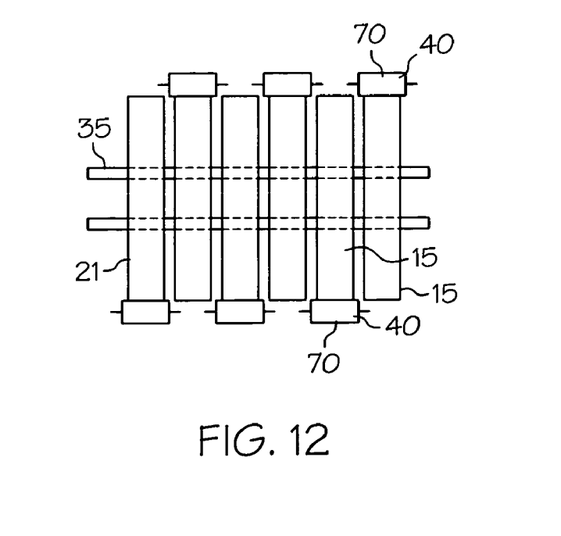
FIG. 12 is an alternative embodiment having frictional slide rollers.

FIGS. 11 and 12 illustrate alternative embodiments in which a drive device 40 may include friction drive rollers 70. Rollers 70 may be in mechanical communication with the mount 21 of a crimping section 15. As the rollers 70 rotate, they may drive one or more of the mounts 21, resulting in a crimping action. The blade constraining members 35 shown in FIG. 12 again remain stationary or environmentally fixed in the embodiment. The rollers 70 may be parallel to and may slide in a direction parallel to the longitudinal axis of the crimping device. This may simplify the control and operation of embodiments having multiple crimping sections 15.

Any of the embodiments described herein may be used to shape an article that may be placed in the chamber 28. Generally, the device may be used for manipulating an article and specifically, for applying a radial inward force to an article. For example, an article may be placed within a chamber 28. If the device includes multiple crimping sections 15, the article may be placed within the chambers 28 of the multiple crimping sections 15. The mount 21 of each crimping section 15 may be rotated independently, causing the blades 20 of each crimping section 15 to contact and reduce the size of the article. The chamber 28 of each crimping section 15 may be reduced as desired to impart a shape to the article. After shaping, the article may have a uniform diameter, or may have a contoured, tapered or undulating shape.

A reduction in the diameter of an article, such as a stent or other medical device, as a result of processing the article using the above-described device 10 may occur as part of a precrimping step, or may occur while crimping a stent about a catheter, and desirably, crimping a stent onto a balloon disposed about a catheter.

The inventive device 10 may also be used to crimp discrete sections or longitudinal portions of an article. For example, the device 10 may be used to crimp multiple discrete marker bands which are disposed about a catheter. To that end, the invention is directed to a method of crimping marker bands by using the inventive apparatus to selectively crimp the marker bands.

In various embodiments, the cross-sectional shape of a chamber 28 may be modified by modifying the shape of the blades 20. A contacting surface 32 of a blade 20 may be shaped to impart a shape to the chamber 28.

Figure 13:
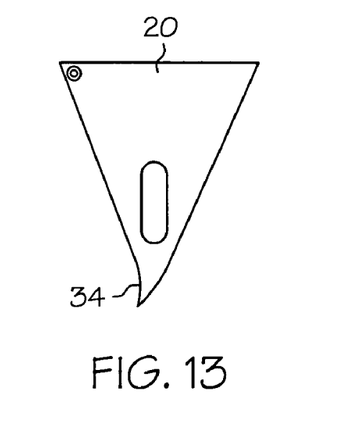
FIG. 13 shows an embodiment of a blade.

FIG. 13 shows an embodiment of a blade 20 having a contoured contacting surface 32. The contoured contacting surface 32 may have curvature. As shown, a plurality of blades 20 having a contoured contacting surface 32 may form a chamber 28 having a circular cross-section during at least a portion of blade 20 travel.

In some embodiments, all of the blades 20 may have the same shape. In some embodiments, some of the blades 20 may have a first shape, while blades may have another shape. In some embodiments, each blade 20 may be shaped differently from all of the other blades included in the crimping section 15. The contacting surface 32 of each blade 20 may be shaped to impart any suitable shape to the chamber 28. The cross-section of a chamber 28 may be a regular polygon, a non-regular polygon, a curved shape such as a circle or ellipse, or any other suitable shape.

The contacting surface 32 of a blade 20 may be shaped to impart a shape to the chamber 28 as described in U.S. patent application Ser. No. 10/788,088, the entire disclosure of which is incorporated herein by reference.

Other blade shapes such as those described in commonly assigned U.S. Pat. No. 6,360,577 incorporated by reference herein, may be employed as well. For example, the blades 20 may include a beveled portion or inner end so as to mesh with adjacent blades, and an outer end which is displaced from the chamber 28 or iris. The blades 20 may be shaped with a curved contacting surface as well to form a chamber having a substantially circular cross-section or iris through at least a portion of blade 20 travel.

In an embodiment of the device 10 having multiple crimping sections 15, each crimping section 15 may have a chamber 28 having any suitable cross-sectional shape.

Figure 14:
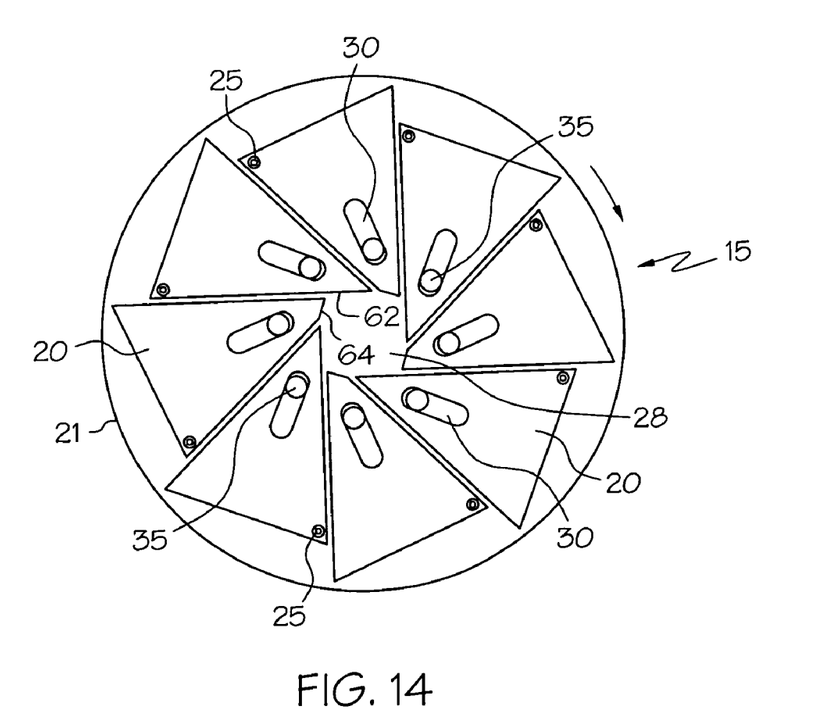
FIG. 14 shows another embodiment of the device.

FIG. 14 shows another embodiment wherein a portion of the blades 20 may have a planar contacting surface 62, and a portion of the blades 20 may have an alternately shaped contacting surface 64. The blades 20 having an alternately shaped contacting surface 64 may extend a lesser distance toward the central longitudinal axis of the device 10. Thus, the blades 20 having a planar contacting surface 62 may contact an article placed within the chamber 28 before the blades 20 having an alternately shaped contacting surface 64 contact the article. This arrangement may facilitate the crimping of a stent around an artifact such as a radiopaque marker. This arrangement may also facilitate balloon folding when using the device to shape balloons, especially when a balloon includes cutting blades, such as the balloons described in U.S. patent application Ser. No. 10/423,598, the entire disclosure of which is incorporated herein by reference, as the blades 20 having an alternately shaped contacting surface 64 may apply less pressure to portions of an article within the chamber 28.

Any embodiment of the inventive device may also be provided with soft-edge blades which may be useful when shaping an article that is fragile or includes a coating. A soft-edge blade may have a contacting surface made from a polymeric material, or may have a polymeric coating or pad applied to a contacting surface. Any polymeric material may be used, such as nylon, or Delrin® or Teflon® available from DuPont. Other examples include elastomers and more specifically block copolymer elastomers such as Pebax® available from Elf Atochem, Hytrel® available from DuPont, SES, SIS, SBS, SIBS, SEBS or combinations thereof. In some embodiments, a soft-edge or pad may be made from a silicone rubber suitable for biomedical use, such as Silastic® BioMedical Grade Liquid Silicone Rubber available from Dow Corning. Desirably, a silicone rubber may have a low durometer hardness of 30 A or less, such as Silastic® 7-6830, and be suitable for use with the device during warming or cooling as herein described.

In some embodiments wherein a blade 20 may include a first contacting surface 32 and a second contacting surface 34, a soft-edge or pad may be provided for one of the contacting surfaces, or for both contacting surfaces.

The inventive apparatus may also be incorporated into a blow molding tool to provide a variable size balloon mold as described in U.S. Pat. No. 6,360,577 and U.S. patent application Ser. No. 10/788,088. Thus, in various embodiments, the inventive device may be used as a variable size and/or variable shape balloon mold.

A balloon precursor or preform prepared through any suitable technique known in the art may provided. The preform, such as a tube or parison, may be placed in a chamber 28 or multiple chambers 28, and the chambers 28 may be sized according to the desired balloon dimensions. Pressurized inflation fluid may be applied to the interior of the preform, thus blowing or inflating a balloon. The preform may inflate until it contacts the contacting surfaces 32 that form the chamber 28 along the length of the device or until a desired shape has been accomplished. The contacting surfaces 32 of the blades 20 may contact the balloon, impart the shape of the chamber 28 to the balloon and restricting the balloon from further expansion. Thus, the inflated shape of the balloon may be determined by the shape of the chamber 22. After the balloon is fully shaped, the inflation fluid may be removed. The blades 20 may be moved to increase the size of the chamber 22, allowing the balloon to be removed.

The present invention also contemplates a method of reducing the diameter of an article, such as a stent, in cross-section. The method includes the steps of providing a device 10 as herein described for applying an inward force to the article, the device 10 including at least two crimping sections 15, each crimping section 15 including a plurality of blades 20, the blades 20 of each section 15 arranged to form a chamber 28; placing an article within the chamber 28 of both sections 15; and actuating each crimping section 15, desirably independently, such that the blades 20 move so as to reduce the size of the chamber 28 and apply an inward force to the article. Desirably, the device includes three or more crimping sections.

In some embodiments of the invention, the blades 20 may be actuated by rotating the mount 21 relative to the blade constraining members 35. Therefore, in some embodiments, the mount 21 may be rotated while the blade constraining members 35 remain fixed in place. In some embodiments, the mount 21 may remain fixed in place and the blade constraining members 35 may be rotated. Desirably, when blade constraining members 35 may be rotated, they may be rotated about the central axis of the chamber 28.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. An apparatus for applying an inward force to a medical device comprising:
    a blade constraining member;
    a first mount rotatable with respect to the blade constraining member;
    a first plurality of blades arranged to form a first chamber whose size may be varied by rotating the first mount with respect to the blade constraining member, each blade of the first plurality of blades pivotally connected to the first mount;
    a second mount rotatable with respect to the blade constraining member;
    a second plurality of blades arranged to form a second chamber whose size maybe varied by rotating the second mount with respect to the blade constraining member, each blade of the second plurality of blades pivotally connected to the second mount;
    wherein the blade constraining member is engaged with at least one blade from the first plurality of blades and with at least one blade from the second plurality of blades.

2. The apparatus of claim 1, further comprising a first drive device arranged to rotate the first mount with respect to the blade constraining member.

3. The apparatus of claim 2, further comprising a second drive device arranged to rotate the second mount with respect to the blade constraining member.

4. The apparatus of claim 1, wherein the blade constraining member is slidably engaged with at least one blade from the first plurality of blades and with at least one blade from the second plurality of blades.

5. The apparatus of claim 4, wherein a blade from the first plurality of blades further comprises an aperture, a blade from the second plurality of blades further comprises an aperture, and the blade constraining member extends through the aperture of the blade from the first plurality of blades and through the aperture of the blade from the second plurality of blades.

6. The apparatus of claim 4, wherein a blade from the first plurality of blades further comprises a slot, and the blade constraining member translocates within the slot as the first mount is rotated with respect to the blade constraining member.

7. The apparatus of claim 1, further comprising a plurality of blade constraining members, wherein each blade constraining member is engaged with one blade from the first plurality of blades and with one blade from the second plurality of blades.

8. The apparatus of claim 1, wherein the first mount and first plurality of blades comprise an independently operable discrete section, the second mount and second plurality of blades comprise another independently operable discrete section, further comprising a third independently operable discrete section.

9. The apparatus of claim 8, further comprising 4 to 80 independently operable discrete sections.

10. The apparatus of claim 9, further comprising a drive device for each independently operable discrete section.

11. The apparatus of claim 1, wherein the first plurality of blades includes three or more blades.

12. The apparatus of claim 1, wherein the first plurality of blades includes eight blades.

13. The apparatus of claim 1, wherein the first plurality of blades includes 16 or more blades.

14. An apparatus for applying an inward force to a medical device comprising:
 a mount;
 a plurality of blades arranged to form a chamber whose size may be varied, each blade pivotally connected to the mount; and
 at least one blade constraining member;
 wherein at least one blade comprises a slot that is slidably engaged with the blade constraining member, the slot having a non-cylindrical opening with a lengthwise axis, a pivot point of the blade being offset from the lengthwise axis; and the mount is arranged to rotate with respect to the blade constraining member.

15. The apparatus of claim 14, wherein the slot comprises an aperture, and the blade constraining member extends through the aperture.

16. The apparatus of claim 15, wherein the blade constraining member translocates within the slot as the mount is rotated with respect to the blade constraining member.

17. The apparatus of claim 14, wherein one blade constraining member is provided for each blade, and each blade is slidably engaged with a blade constraining member.

18. The apparatus of claim 14, wherein the chamber has a length of 2 mm or less.

19. The apparatus of claim 14, further comprising a motorized drive device arranged to rotate the mount.

20. The apparatus of claim 19, wherein the motorized drive device comprises an electric motor, a linear actuator, a hydraulic drive system or a pneumatic drive system.

21. The apparatus of claim 19, wherein the mount comprises a gear that meshes with a drive gear of the motorized drive device.

22. An apparatus for applying an inward force to a medical device comprising:
 a plurality of blade constraining members;
 a first mount having a plurality of first blades arranged to form a first chamber, each first blade being pivotally attached to the first mount;
 a second mount having a plurality of second blades arranged to form a second chamber, each second blade being pivotally attached to the second mount;
 each blade having a slot;
 each blade constraining member passing through the slot of a first blade and through the slot of a second blade;
 wherein the size of the first chamber maybe adjusted by rotation of the first mount relative to the blade constraining members; and
 wherein the size of the second chamber may be adjusted by rotation of the second mount relative to the blade constraining members.

23. A method of reducing the size of a medical device, the method comprising the steps of:
 providing an apparatus for applying an inward force to a medical device, said apparatus comprising a plurality of blades arranged to form a chamber; each blade being pivotally secured to a mount; at least one blade comprising a slot that is slidably engaged with a blade constraining member, the slot having a non-cylindrical opening with a lengthwise axis, a pivot point of the blade being offset from the lengthwise axis; wherein the size of the chamber may be adjusted by rotating the mount with respect to the blade constraining member;
 placing a least a portion of a medical device within said chamber; and
 rotating the mount with respect to the blade constraining member to reduce the size of the chamber, thereby reducing the size of at least a portion of the medical device.

24. A method of reducing the size of a medical device, the method comprising the steps of:
 providing an apparatus for applying an inward force to a medical device, said apparatus comprising a plurality of first blades arranged to form a first chamber; each first blade being pivotally secured to a first mount at least one first blade being slidably engaged with a blade constraining member; wherein the size of the chamber may be adjusted by rotating the first mount with respect to the blade constraining member, the apparatus further comprising a plurality of second blades arranged to form a second chamber, each second blade being pivotally secured to a second mount; at least one second blade being slidably engaged with said blade constraining member; wherein the size of the second chamber may be adjusted by rotating the second mount with respect to the blade constraining member;
 placing a portion of a medical device within said first chamber and a portion of the medical device within said second chamber;
 rotating the first mount with respect to the blade constraining member to reduce the size of the first chamber thereby reducing the size of at least a portion of the medical device; and
 rotating the second mount with respect to the blade constraining member to reduce the size of the second chamber, thereby reducing the size of a second portion of the medical device.

25. The method of claim 24, wherein the first chamber may be adjusted independently from the second chamber.

26. The method of claim 23, wherein the medical device is a stent.

27. The method of claim 26, wherein the stent is disposed about a medical balloon, and the medical balloon is disposed about a catheter.

28. The method of claim 23, wherein the mount is rotated relative to the blade constraining member by a drive device.

29. The method of claim 23, further comprising the step of cryogenically cooling the blades.

* * * * *